United States Patent [19]

Maes

[11] Patent Number: 4,777,130

[45] Date of Patent: Oct. 11, 1988

[54] ISOLATION OF MYCOBACTERIAL A 60 ANTIGEN FOR DIAGNOSTIC PURPOSES

[75] Inventor: Roland F. Maes, Strasbourg, France

[73] Assignee: Andra Biologicals, Strasbourg, France

[21] Appl. No.: 678,470

[22] Filed: Dec. 5, 1984

[51] Int. Cl.$^4$ .................. G01N 33/53; G01N 33/566; C12Q 1/02; C12Q 1/06

[52] U.S. Cl. .......................................... 435/7; 435/29; 435/259; 435/803; 435/820; 435/863; 435/864; 435/866; 436/501; 436/811; 424/87; 424/92

[58] Field of Search ................... 436/501, 811; 435/4, 435/7, 29, 863, 864, 866, 259, 803, 820; 424/87, 92, 95

[56] References Cited

U.S. PATENT DOCUMENTS

| | | | |
|---|---|---|---|
| 3,888,837 | 6/1975 | Tsumita et al. | 435/866 X |
| 4,351,761 | 9/1982 | Gaafar | 424/92 X |
| 4,410,660 | 10/1983 | Straus | 424/87 X |

OTHER PUBLICATIONS

Engers, H. D. et al., Infect. Immun, 51:718–720 (1986).
Kolk et al., Clin. Exp Immunol. 58:511–521 (1984).
Hewitt, J. et al., Journ. Immunol. Methods 55:205–211 (1982).
Closs, O. et al., Scand. Journ. Immunol. 12:249–263 (1980).
Harboe et al., Scand. Journ. Immunol. 9:115–124 (1979).
Grange, J. M. et al., Biological Abstracts 71(4), Abstracts #24441, #25119, (1981).

*Primary Examiner*—Robert J. Warden
*Assistant Examiner*—Jack Spieger
*Attorney, Agent, or Firm*—William J. Daniel

[57] ABSTRACT

A 60-like antigens isolated in a one-step reaction from the bacterial cytoplasma of Mycobacteria are useful for the production of diagnostic tests.

5 Claims, 2 Drawing Sheets

ISOLATION OF MYCOBACTERIAL A 60 ANTIGEN FOR DIAGNOSTIC PURPOSES

FIELD OF THE INVENTION

This invention relates to the isolation of A 60-like antigens derived from Mycobacteria and their immunologically active fragments and use thereof for diagnostic test purposes and the production of antibodies against the same.

SUBJECT OF THE INVENTION

Mycobacteria, belonging to the order Actinomycetales, are grampositive bacteria pertaining to the super-group CMN, which stands for Corynebacterium, Mycobacterium and Nocardia.

The mycobacteria are subdivided into several groups. Three of these groups are differentiated according to the physico-chemical conditions under which they synthesize carotenoids. These three groups are the photochromogens (group I), the scotochromogens (group II) and the nonchromogens (group III). A fourth group consists of the "rapid growers". The mycobacteria that produce lepra (leprosy) in mice and in humans are not included in these four groups.

Another classification system for these bacteria depends upon their pathogenicity since only some Mycobacteria belonging to these four groups are considered pathogenic. The major representatives of the group responsible for the typical tuberculosis in man and bovine, in the sense of "typical" etiologic agents, are *M.tuberculosis* and *M.bovis*. "Atypical" agents, i.e., conditional pathogens of tuberculosis, are represented by *M.avium* (strictly pathogenic for birds), *M.intracellulare*, *M.scrofulaceum*, *M.xenopi*, *M.ulcerans*, and *M.kansasii*. These latter agents, belonging to the three major Mycobacterial groups, may in addition cause arthritis, dermatitis and extra-pulmonary tuberculosis. Human leprosy is caused by *M.leprae*.

Conventional diagnosis of leprosy and tuberculosis is based on cutaneous tests using inactivated bacterial extracts namely lepromin and tuberculin. These extracts contain impurities that may cause allergic reactions. Cutaneous tests using them are, furthermore, of long duration (1 to 3 days) and imprecise in result in that they do not allow the monitoring of the evolution of a disease or the effects of any chemio-therapeutic intervention or treatment. Observation of a changing reactivity of the patient over the course of time is also not possible with these tests that give a simple "yes or no" answer.

Diagnostic tests using the serum of the patient and based on specific reagents would allow a more refined epidemiological survey, a speed of diagnosis much superior to that of cutaneous tests and would avoid discomfort to the patient.

BACKGROUND OF THE INVENTION

Numerous species of Mycobacteria exist, some non-pathogenic, some conditionally pathogenic, some inducing an atypical tuberculosis, and some inducing other diseases such as leprosy, arthritis and dermatitis.

These bacteria are complex organisms. *M.tuberculosis* was thought initially to be composed of 11 major antigens. However, more recent investigation has shown the number of its antigens to be much higher. Some of these antigens are common to several genera, i.e., they show an immunological cross-reactivity between organisms belonging to the super-group Corynebacterium-Mycobacterium-Nocardia. Other antigens are common to all the members of the genus Mycobacterium and a third group of antigens is species-specific.

The interest of investigators in this field was directed toward the mycobacterial species-specific antigens since their use would allow a taxonomic frame for the mycobacteria and also on those antigens whose antigenic power was promising for the elaboration of vaccines.

In 1980, it was recognized (Closs et al (1980): Scand. J. Immunol. 12, 249–263) that *M.bovis* (attenuated strain BCG) was composed of a large number of antigens revealed through a bidimensional or cross immunoelectrophoresis analyses. These antigens exhibition identifiable precipitation pattern upon such analysis, and these patterns have been assigned a characteristic antigen number. The antigen identified as A 60 was of particular interest in that it was thermostable, a potent immunogen and common —without being identical—to all analyzed Mycobacteria, extending in fact to the whole of the super-group CMN. In particular, A 60 of *M.bovis* and A 7 of *M.leprae* were found to be cross-reactive (Harboe et al. (1979) Scand. J. Immunolog. 9, 115–124).

SUMMARY OF THE INVENTION

In accordance with the invention, high molecular weight antigenic material exhibiting a precipitation pattern when subjected to CIE analysis corresponding to the characteristic CIE pattern of antigen A 60, according to the identification system of Closs et al have been recovered from a number of different Mycobacteria and isolated in substantially pure form. For convenience, the thus-isolated antigenic material is referred to as "A 60-like antigen". The thus-isolated A 60-like antigen has been used to establish that patients suffering diseases caused by various Mycobacteria, including typical human and bovine tuberculosis, atypical tuberculosis and the like carry in their sera antibodies which are antibodies against such A 60-like antigens. Based on this discovery, A 60-like antigen has been employed to detect the presence of such antibodies in the sera of patients suffering from such diseases following known immunological diagnostic procedures in which, in general, the A 60-like antigen is brought into contact with the sera for complexation with any antibodies contained therein and such complexation detected in various known ways including radiographic tracing as in recognized RIA techniques, enzymo-labelling, as in recognized EIA techniques, and the agglutination of sensitized carrier particles. The A 60-like antigen has also been used for the production of both polyclonal and monoclonal antibodies by injection of the antigen into test animals and recovery of antibodies produced thereby. Further, the A 60-like antigens can be fragmented by the splitting action of known protease enzymes and the immunologically-active fragments from such splitting reaction can be recovered and isolated and used to elicit an immunological response.

BRIEF DESCRIPTION OF THE DRAWINGS

FIG. 2 shows the immunoelectrophoresis results of exclusion chromography of a cytoplasmic sample of

Figure 1:
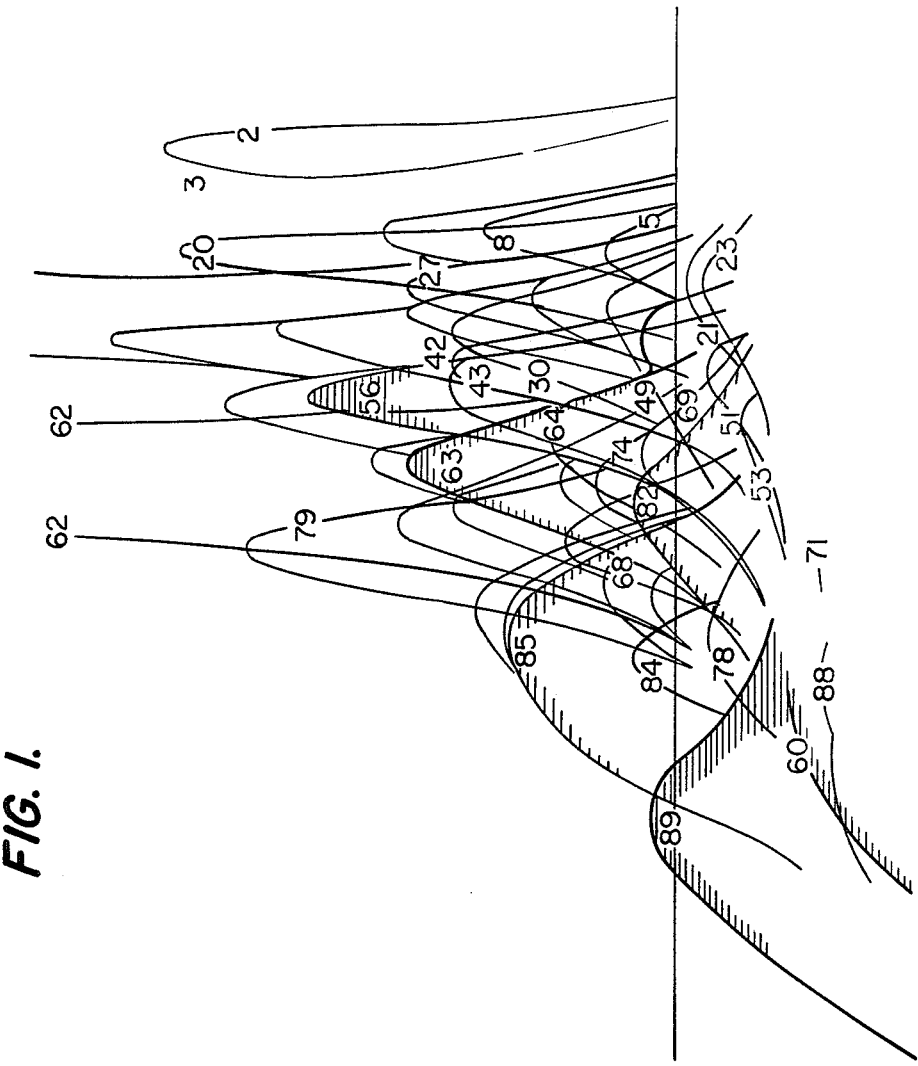
FIG. 1 is an illustration of the reference system for extracellular antigens of *M.bovis* BCG obtained by bidimensional immunoelectrophoresis and colored with Coomassie blue, the second dimension occuring through a gel containing whole anti-BCG serum.
Figure 2:
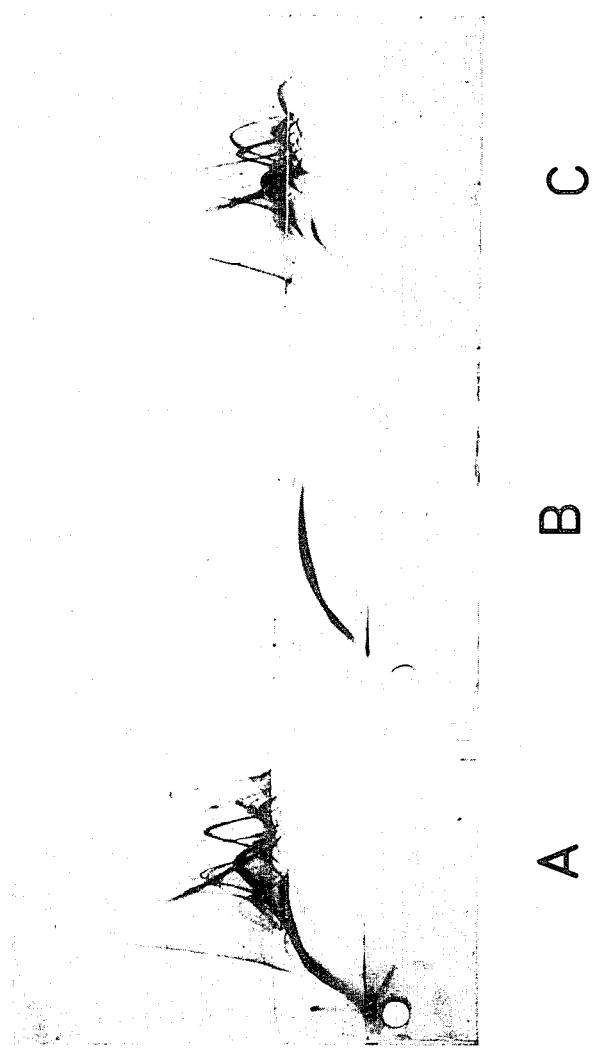

*M.bovis* BCG in which A is the starting cytoplasma, B is an exclusion peak constituted substantially entirely of A 60-like antigen, and C is the inclusion peak containing all other proteinaceous matter.

DETAILED DESCRIPTION OF THE INVENTION

The bacterial strains used in this study were obtained mainly from the National Collection of Cultures of Microorganisms, C.N.C.M., Pasteur Institute, 25, rue du Docteur Roux, 75724 Paris FRANCE. Another source was the Station experimentale d'aviculture B.P. 9, 22440 PLOUFSAGAN, FRANCE.

The bacteria (with the exception of M.leprae are multiplied in Dubos medium supplemented with 5% horse serum decomplemented through heating at 56° C. during 30'. They are collected at the end of the growth phase through centrifugation and the bacterial walls are disrupted by compression and decompression in a French cell (Aminco instruments, Silver Spring, Md., U.S.A.) at 8000 p.s.i. and 4° C.

A 60-like antigen of various Mycobacteria is easily isolated and purified in a one-step chromatographic procedure. Homogenates of the various Mycobacteria are centrifuged at 20,000 r.p.m. for 10' at 4° C. to eliminate cellular debris from the supernatant containing the cytoplasm. When a cytoplasmic sample of *M.bovis* BCG is subjected to bidimensional immunoelectrophoresis, the various antigenic constituents thereof are fractionated in a pattern in the manner of Closs et al as illustrated in FIG. 1. Specifically, the reference pattern of FIG. 1 is obtained by subjecting a test sample, about 24 μl of the starting cytoplasmic sample in 10 μl barbital buffer, to electrophoresis in two directions or dimensions with the second direction of electrophoresis being through an agarose gel containing whole anti-BCG serum obtained commercially from Dako of Denmark, and then to coloring by Coomassie blue. FIG. 2 shows the results of molecular sieve chromography obtained by passing a cytoplasmic sample of *M.bovis* BCG consisting of 16.5 mg protein in 1 ml on a Sepharose 6B column (Trademark for spherical agarose gel beads with exclusion limits of about $4\times10^6$ daltons for proteins and $1\times10^6$ daltons for polysaccharides sold by Pharmacia Fine Chemicals AB). The starting sample is indicated at A and has a proteinic pattern of immunoelectrophoresis similar to that of FIG. 1; the exclusion peak is indicated at B which consists substantially of A 60-like antigen as shown by its immunoelectrophoretic location, and the inclusion peak is at C which includes all other proteinaceous matter, i.e. all other antigens present in the sample. If desired, peak B, in case the presence of some containments is still observed after immunoelectrophoretic analysis may be re-chromatographed on the same column, which will yield A 60-like antigen in an immunochemically homogeneous form.

A 60-like antigen purified by bichromatography on a Sepharose 6B column has been chemically analyzed. It is composed of 57% protein and 43% polysaccharides. Its unit of reference was established as follows: 1 unit A 60-like antigen is the quantity of electrophoretically purified and Coomassie blue colored antigen whose absorbance in solution at 530 nm is:

$$A^{1}\ cm/_{530}=0.1$$

This spectrophotometric unit corresponds to 1.5 μg of the proteinic component and to 1.23 μg of the polysaccharidic component. It corresponds thus to 2.45 μg of cytoplasmic A 60.

Antigen A 60 of *M.bovis* is the slowest migrating component of the bacterial cytoplasm into the electrophoretic field (1% agarose in Tris-barbital buffer 0.02M at pH 8.6; 8 volts/cm during 1 h at 15° C. in the first dimension and 3 volts/cm during 18 h at 15° C. in the second dimension; detection of the proteinic components by Coomassie blue). The bulk of the work was accomplished with *M.bovis* attenuated strain-Calmette-Guerin Bacillus (BCG). After having determined the optimal conditions for isolation of A 60-like antigen, the same material, recognized by its immunoelectrophoresis location was isolated, through the same simple molecular-sieve chromatographic technique, from a photochromogen (group I, *M.kansasii*), a scotochromogen (group II, *M.scrofulaceum*), a nonchromogen (group III, *M.xenopi*) and a "rapid grower" (group IV, M.chelonei). To these representative of the various Mycobacteria groups that induce some sort of tuberculosis (*M.xenopi* and *M.scrofulaceum* are usually non-pathogenic) was added *M.leprae*, which had been armadillo-grown, and purchased under the form of lepromin.

About 15 mg of proteins liberated from the cytoplasm of each of these bacteria in 1 ml buffer (CaCl 2-0.04M; Mg-acetate - 0.015M; Tris-HCl - 0.02M; pH - 7.4) were treated for 10' at 37° C. with 10 units of RNase, then immediately chromatographed twice on a Sepharose 6B column and the A 60-like antigens from the 6 starting Mycobacteria were brought therewith to immunochemical purity. Samples applied to the column were 1 ml, bed volume of Sepharose was 10 ml and void volume was 3.5 ml.

The A 60-like homologous proteins extracted from these 6 Mycobacteria were recognized by their immunoelectrophoretic behavior. All Mycobacterial species analyzed contained this protein in large quantities. The A 60-like antigen of *M.leprae* was recognized to be the principal antigen of lepromin, also named A 7 in former reference systems.

The production of polyclonal murine antibodies against the isolated A 60-like antigens went according to known procedures. Such procedures include recovery from the serum or spleen of animals inoculated with the antigen or other techniques. Briefly, Balb/c mice were primed with Pristane (0.50 ml I.P.). Fifteen days later, one ml of a 10% suspension of an aqueous solution of the antigen (10 mg/ml) in Freund incomplete adjuvant was inoculated interperitoneally. After 15 days, 2 weekly intraperitoneal re-inoculations took place. The mice produced therewith an ascites that secreted large amounts of antibodies. The mice were punctured and drained every 3 days, and they usually died after the 5th to 6th drainage, from dehydration.

Monoclonal antibodies were obtained in Balb/c mice according to known procedures. (Köhler, G. and Milstein, C. Continuous cultures of fused cells secreting antibody of predefined specificity. Nature, 1975, 256, 495–497).

Fifty-one clones each secreting an antibody specific for M.bovis A 60-like antigen—strain BCG—were isolated, and three to six clones for each of the five other isolated A 60-like antigens.

Polyclonal antibodies are a heterogenous population of antibodies directed against all epitopes available in an antigen. A monoclonal antibody is a homegenous population of antibodies directed against one single epitope of an antigen. This epitope may or may not be shared by other homologous antigens. In our case, a monoclonal antibody may be specific for a mycobacterial strain, subspecies, species, genus.

The availability of polyclonal antibodies, of monoclonal antibodies and of a large supply of A 60-like antigens of high purity isolated as described above allowed the development of several diagnostic tests. Their use will be exemplified in the following examples.

EXAMPLE I

120 μg of antigen-like A 60 in 120 μl phosphate buffered saline, pH 7.2 (PBS) were incubated with 3 μl of I 1225 (300 uCi and 10 μl of chloramine T (6.5 mg/ml in phosphate buffered saline pH 7.2) during 3 minutes at 20° C. The reaction was stopped by addition of 10 μl sodium metabisulfite (8.45 mg/ml in phosphate buffered saline pH 7.2). The final volume was brought to 200 μl with PBS and chromatographed on 2 ml of Sepharose 6B. The exclusion peak containing I 125 labeled A 60-like antigen was stored in the presence of 0.2% albumin and 0.02% NaN3.

A radioimmunological (RIA) test was therewith developed for the determination of minimal amounts of antibodies. Protein A from *Staphylococcus aureus* was purchased from Pharmacia (Uppsala, Sweden). This protein has the property to specifically combine with human and mouse IgG even if antigen is bound to them. The protein A was absorbed on the walls of polystyrene tubes. I 125 labeled A 60-like antigen (about 3000 CMP per μl) was added to unknown amounts of antibodies and the resulting complex was thereafter contacted with the protein A carrier. After suitable incubation allowing attachment of the antibodies to the protein A, the amount of radioactivity attached to the walls of the polystyrene was measured.

This classical radioimmunological assay (RIA) test repeated with the various polyclonal antibodies and the 6 labeled antigens available established that all polyclonal antibodies obtained by the injection of these antigens as vaccines interreacted to a large extend (7% to 100%) with all A 60-like labeled antigens applied in an RIA test.

It was discovered from further tests that the radioactive labeled A 60-like antigens competed to a variable extent with Purified Protein Derivative (PPD) which is a purified preparation of tuberculin (i.e., an extract of BCG), and surprisingly also with lepromin (an extract of *M.leprae*) and with Leoprosy-derived-corynebacteria (L.D.C.), for complexing with the 6 polyclonal antibodies tested.

This indicates that A 60-like antigens of various Mycobacteria species, including those that do not provoke tuberculosis, contain at least one epitope common to all species composing the CMN super-group and against which antibodies are made. An exploration of the specificity of the various monoclonal antibodies obtained was also made by the same RIA technique. Most of them were found to be overlapping to some extent. However, one clone secreting an antibody absolutely specific for A 60-like antigen of *M.kansasii* and for A 60-like antigen of *M.scrofulaceum* could be isolated as well as four (out of 51 clones) for A 60-like antigens of *M.bovis*. On the other hand, clone 31 was found to secrete antibodies that reacted with all A 60-like antigens presented. It has a very large spectrum of immunological activity. No clones secreting antibodies specific for the other Mycobacteria species were obtained, no doubt because the initial number of antibody secreting clones isolated was too small.

EXAMPLE II

The A 60-like antigen of *M.bovis* was adsorbed to the walls of polystyrene microcups (96 per plate) at pH 9.6 in 0.1M 0.1 M carbonate buffer. After adsorption, the wells were filled with a solution 0.1% in albumin in phosphate buffered saline at 4° C. during 18 h, then the wells were washed with an 0.05% Tween 20 solution in PBS and the wells were finally drained and stored dry in the cold (4° C.). It was found that the A 60-like antigen adsorbed to the walls and kept dry could be stored at 4° C. during at least 4 months without any observable degradation in its immunological properties.

Goat antibodies against human IgG were purified by affinity chromatography and labeled with peroxidase following classical procedures. This reagent has the dual function to adsorb to human IgG through its antibody moeity and to allow a colored enzymatic reaction through its peroxidase moeity.

An enzymo-immunoassay (EIA) was thereby prepared, where human antibodies to A 60-like antigen contained in a test sample, e.g., patient sera, were specifically adsorbed on the sensitized walls of the microcup by complexing with the adsorbed A 60 antigen. After washing with Tween-PBS, the presence of the human specific antibodies that attach to the A 60-like antigen on the wells is revealed by peroxidase-labeled anti-human IgG antibodies. These antibodies will attach to any human IgG present and, after washing, the presence of these antibodies is analyzed by a color reaction based on the enzymatic activity of its peroxidase moeity.

As a parallel test, the same A 60-like antigen (500 μg/ml) was adsorbed to 20% suspension of latex particles (0.8 mu in diameter) in 0.1 m glycine buffer at pH 8.0. After washing the latex particles, verification that agglutination would take place in the presence of a dilution of anti-A 60 antiserum in PBS was accomplished by mixture of 50 ul of a dilution of a polyclonal antibody on a slide. After 5 minutes of slow rotation, the limit of dilution of the antibody was recognized to be 1/1200. Competition between the sensitized latex and free A 60-like antigen for this dilution of antibody showed that 2.6 μg/ml of free A 60-like antigen were needed to inhibit the latex agglutination induced by the diluted antibody.

These two qualitative tests were used to verify the presence of antibodies in the sera of patients who were known to be positive for tuberculosis according to a standard cutaneous test. In order to avoid non-specific reactions of the sera with the latex sensitized with A 60-like antigen, the sera had to be diluted 6 times in PBS before use.

A correlation of 98% was found for positive reactions between cutaneous tests and EIA just described.

Sera shown to be negative by the standard tuberculin test proved negative by this EIA, although the EIA did produce some false positives (97% correct).

The rapid latex slide agglutination test was normally slightly less sensitive. It picked up only 94% of the positives. However, all cutaneous negatives were also negative with the slide test.

These results indicate that antibodies against the A 60 component of Mycobacteria are present in large quantities in the serum of patients that showed positive for tuberculosis in a cutaneous tuberculin test and that diagnostic tests—latex agglutination or EIA—based on recognition of such antibodies in serum are valuable diagnostic tools.

EXAMPLE III

Several proteases are available to the art in order to break proteins into fragments. The most popular enzymes used for this purpose are trypsin, papain, chymotrypsin and subtilisin, but more esoteric enzymes may be applied as well as chemicals such as CNBr and beta-propiolactone. They split the protein at various specific aminoacid junctions producing thereby different fragments. Experiments were conducted to verify that the splitting with trypsin does not occur precisely at an immunologically important epitopic site. This was done by treating A 60 antigen of *M.bovis* with the protease, and verifying therefore the ability of the fragments to compete for *M.bovis* antibodies with I 125 labeled antigen in an RIA-test, as in example I.

Here, trypsin was suitable and no additional protease was used.

A 60 antigen of *M.bovis* (15 mg in 15 ml) was treated with trypsin according to known procedures. Briefly, trypsin attached to cellulose via CNBr was incubated with the solutions of A 60 antigen in a buffer constituted of Hank's solution at pH 7.2. After 3 hours at 37° C., the cellulose-bound trypsin was removed by centrifugation.

The solution of degraded A 60 antigen of M.bovis was dialysed against an 0.1M glycine buffer at pH 8.0, then contacted with latex particles (0.8 mu in diameter) as in example II. A latex agglutination test was thereby produced that proved identical in sensitivity to a test developed with the intact A 60 antigen. Its superiority resided in the fact that the tendency to spontaneous unspecific aggregation of the latex particles in the presence of serum components was substantially reduced.

EXAMPLE IV

The presence of Mycobacteria in the spittle of diseased people is assessed by mixing the sputum with fluorescently-tagged antibodies on a microscope slide. After suitable incubation, the slide is washed, is mounted and is viewed in a fluorescent microscope.

This diagnostic test is too sophisticated to be applied in those geographic areas where the disease is most common; i.e. Spain, Southern Italy, North Africa.

Latex at a concentration of 10% and pH 8.1 was incubated during 72 h at 45° C. with MAb 31, obtained after cloning a hydridoma secreting antibodies against *M.bovis* A-60 antigen.

After washing, the latex suspension was assayed in a direct aggregation test for the presence of Mycobacteria in sputum. Various concentrations of *Mycobacteria bovis* in sputum of a disease free donor were set up and the fluids appropriately diluted 1:5 with phosphate buffered salive at pH 7.5 were mixed with the sensitized latex. Slow rotation was induced by hand during 3 minutes, after which the degree of aggregation of the sensitized latex was read under incident light. The test was not very sensitive.

The presence of at least 100.000 bacterial/ml sputum was needed to begin to see an aggregation. Nevertheless, despite its insensitivity, the test was functional, and no less sensitive than direct microscopic observation of smears.

A more sensitive detection system of the bacteria was obtained through an EIA, where MAb 31 was adsorbed onto the walls of polystyrene wells as in example II. After incubation of the diluted sputum into the wells, these were washed and the presence of bacteria attached to the MAb 31 antibody was revealed by incubation of the wells with a peroxidase-labeled second antibody and coloration with O-phenylene diamine, as in example II. In this test, the sensitivity was increased and the presence of 10,000 or even less bacteria/ml could be detected.

The above examples show some of the advantages that may be obtained by the use of A 60-like antigen and its fragments for diagnostic purposes in the tuberculosis and leprosis fields, but should not be construed to unduly restrict the field of the invention. It was for instance found that the removal of the sugar moiety from the antigen improved the performance of the latex slide test prepared from it, and that large amounts of specific antibodies could be obtained through the extraction of specific gamma-globulins from the yolk of vaccinated laying hens. Also, A 60-like antigen may be isolated from the supernatant of bacterial cultures, from the ribosomes of the bacteria and from the cytosol. It was also found that ribocomes and ribosomal RNA contaminate the A 60-like antigen prepared from the bacteria cytoplasm; a treatment of the extract with RNAse and DNAse prior to exclusion chromatography considerably improved the purity of the chromatographed product. Sepharose 4B or other molecular-sieve material may be as efficient as Supharose 6B for the separation of A 60-like antigen from other cytoplasmic constituents. Immunologically active fragments of A 60-like may be isolated in ways other than affinity chromatography. Other enzymes than trypsin may prove more efficient in the obtention of the immunologically active fragments. Finally, other diagnostic tests than those here employed such as hemagglutination tests, bentonite tests, Ouchterlony tests, rocket electrophoresis tests and the like will be obvious to the skilled worker in the art.

What is claimed is:

1. A method for the isolation of an antigen from Mycobacteria, which comprises the steps of subjecting the cytoplasm of disrupted Mycobacteria to exclusion chromatography on a column of spherical agarose gel beads having an exclusion limit corresponding substantially to $4 \times 10^6$ daltons for proteins and $1 \times 10^6$ daltons for polysaccharides, wherewith said antigen is substantially excluded from said column, said antigen eluting in said column's void volume as a mixture of protein and polysaccharides separated in substantially immunochemically pure form from all other constituents of said cytoplasm, recovering said void volume, said void volume mixture, when subjected to cross-immunoelectrophoresis, exhibiting an immunoelectrophoretic precipitation pattern corresponding to A 60-antigen of *Mycobacteria bovis* strain BCG.

2. A method of claim 1, wherein said cytoplasm prior to being subject to said exclusion chromatography is treated with RNAse or DNAse to reduce contamination thereof by ribosomes and ribosomal RNA.

3. A method of diagnosing a disease caused by Mycobacteria which comprises the step of contacting an unknown sample of a serum from a patient to be diagnosed for such disease with an antigen isolated according to claim 1 and detecting the occurrence of any complexation of such antigen with antibodies against such antigen present in such serum sample.

4. Antibodies immunologically active against the antigen isolated by the method of claim 1 wherein said antibodies are produced by the process comprising the steps of administering to a test animal an immunologically active amount of said antigen, and recovering said antibodies from said test animal.

5. A method of diagnosing a disease caused by Mycobacteria which comprises the step of contacting an unknown sample of body fluid from a patient to be diagnosed for such disease with antibody according to claim 4, and detecting the occurrence of any complexation of such antibody with a component of said body fluid sample.

* * * * *